United States Patent
Shelton, IV et al.

(10) Patent No.: US 11,202,632 B2
(45) Date of Patent: Dec. 21, 2021

(54) ADJUNCT MATERIAL WITH MATING FEATURES

(71) Applicant: Ethicon LLC, Guaynabo, PR (US)

(72) Inventors: Frederick E. Shelton, IV, Hillsboro, OH (US); Jason L. Harris, Lebanon, OH (US); Michael J. Vendely, Lebanon, OH (US)

(73) Assignee: Cilag GmbH International, Zug (CH)

( * ) Notice: Subject to any disclaimer, the term of this patent is extended or adjusted under 35 U.S.C. 154(b) by 844 days.

(21) Appl. No.: 15/435,997

(22) Filed: Feb. 17, 2017

(65) Prior Publication Data

US 2018/0235629 A1    Aug. 23, 2018

(51) Int. Cl.
*A61B 17/072* (2006.01)
*A61B 17/00* (2006.01)
*A61B 17/115* (2006.01)

(52) U.S. Cl.
CPC .. *A61B 17/07292* (2013.01); *A61B 17/00491* (2013.01); *A61B 17/07207* (2013.01);
(Continued)

(58) Field of Classification Search
CPC ........ A61B 17/07292; A61B 17/00491; A61B 17/1155; A61B 17/07207; A61B 2017/07285; A61B 2017/07278; A61B 2017/07271; A61B 2017/07257; A61B 2017/00884; A61B 2017/00477; A61B 2017/00473; A61B 2017/0023;
(Continued)

(56) References Cited

U.S. PATENT DOCUMENTS

| 6,273,897 B1 * | 8/2001 | Dalessandro .... A61B 17/07207 606/139 |
| 7,143,925 B2 | 12/2006 | Shelton, IV et al. |

(Continued)

FOREIGN PATENT DOCUMENTS

| EP | 1256317 A2 | 11/2002 |
| EP | 2008595 A2 | 12/2008 |

(Continued)

OTHER PUBLICATIONS

Extended European Search Report for EP App. No. 18157201.7 dated May 4, 2018 (10 pages).

*Primary Examiner* — Hemant Desai
*Assistant Examiner* — Mobeen Ahmed
(74) *Attorney, Agent, or Firm* — Mintz Levin Cohn Ferris Glovsky and Popeo, P.C.

(57) ABSTRACT

An adjunct material for use with an end effector for a surgical instrument is provided that has different types of features for mating with the end effector. The adjunct is configured to be releasably retained on a jaw, such as a cartridge or anvil, using a plurality of female features formed thereon. Each female feature is configured to encompass a corresponding at least one of male features formed on the jaw in a clearance fit such that the adjunct is able to move with respect to the jaw at least in a first plane parallel to the tissue-facing surface. The male and female features mate such that the adjunct is not retained in a second plane that is perpendicular to the first plane. The adjunct also includes at least one attachment feature configured to releasably retain the adjunct on the jaw.

22 Claims, 8 Drawing Sheets

(52) U.S. Cl.
CPC . *A61B 17/1155* (2013.01); *A61B 2017/00004* (2013.01); *A61B 2017/0023* (2013.01); *A61B 2017/0046* (2013.01); *A61B 2017/00473* (2013.01); *A61B 2017/00477* (2013.01); *A61B 2017/00526* (2013.01); *A61B 2017/00884* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC   A61B 2017/00004; A61B 2017/00526; A61B 2017/0046
See application file for complete search history.

(56) References Cited

U.S. PATENT DOCUMENTS

| | | | |
|---|---|---|---|
| 7,601,118 | B2 | 10/2009 | Smith et al. |
| 8,317,070 | B2 | 11/2012 | Hueil et al. |
| 8,393,514 | B2 | 3/2013 | Shelton, IV et al. |
| 9,282,962 | B2 | 3/2016 | Schmid et al. |
| 2007/0027554 | A1* | 2/2007 | Biran .................. A61L 31/146 623/23.74 |
| 2009/0001122 | A1* | 1/2009 | Prommersberger .... B29C 39/22 227/176.1 |
| 2012/0241497 | A1* | 9/2012 | Mandakolathur Vasudevan ......... A61B 17/07207 227/176.1 |
| 2012/0241499 | A1* | 9/2012 | Baxter, III ......... A61B 17/0643 227/176.1 |
| 2013/0221065 | A1 | 8/2013 | Aronhalt et al. |
| 2013/0256377 | A1* | 10/2013 | Schmid ............... A61B 17/0644 227/176.1 |
| 2014/0158742 | A1* | 6/2014 | Stopek ............. A61B 17/07207 227/175.1 |
| 2014/0291380 | A1* | 10/2014 | Weaner ............ A61B 17/07207 227/176.1 |
| 2015/0129634 | A1* | 5/2015 | Shelton, IV ...... A61B 17/07292 227/176.1 |
| 2015/0133995 | A1* | 5/2015 | Shelton, IV .......... A61B 17/064 606/219 |
| 2015/0133996 | A1 | 5/2015 | Shelton, IV et al. |
| 2015/0134076 | A1 | 5/2015 | Shelton, IV et al. |
| 2015/0134077 | A1 | 5/2015 | Shelton, IV et al. |
| 2015/0272575 | A1 | 10/2015 | Leimbach et al. |
| 2015/0277471 | A1 | 10/2015 | Leimbach et al. |
| 2015/0282809 | A1* | 10/2015 | Shelton, IV ......... A61B 17/105 227/176.1 |
| 2015/0351758 | A1* | 12/2015 | Shelton, IV ....... A61B 17/0644 606/219 |
| 2016/0089142 | A1 | 3/2016 | Harris et al. |
| 2016/0270793 | A1* | 9/2016 | Carter ................ A61B 17/1155 |
| 2017/0055986 | A1 | 3/2017 | Harris et al. |
| 2017/0367694 | A1* | 12/2017 | Shelton, IV ......... A61B 17/068 |
| 2019/0038280 | A1* | 2/2019 | Shelton, IV ....... A61B 17/0644 |
| 2019/0290275 | A1* | 9/2019 | Carter ................. A61B 17/105 |

FOREIGN PATENT DOCUMENTS

| | | |
|---|---|---|
| EP | 2462880 A2 | 6/2012 |
| EP | 2586380 A1 | 5/2013 |
| EP | 3072457 A2 | 9/2016 |

* cited by examiner

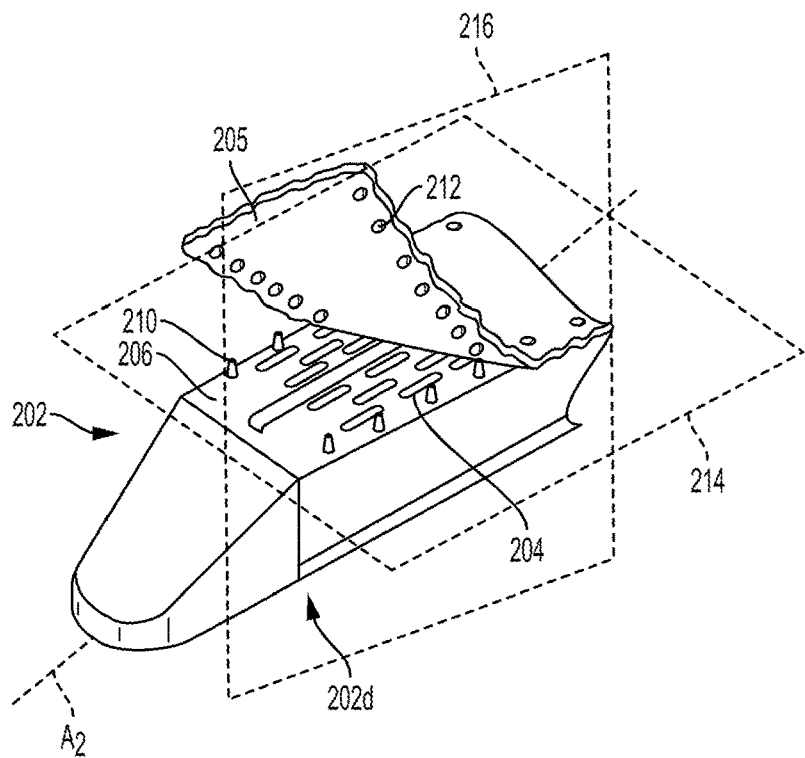
FIG. 8
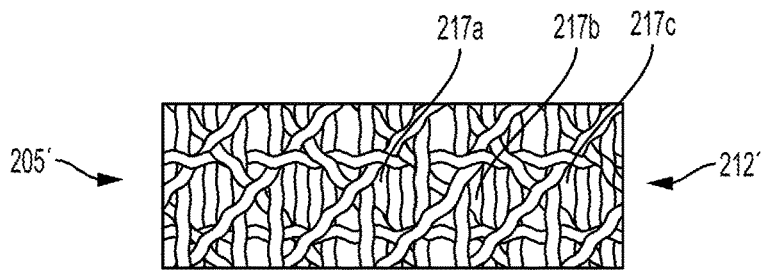
FIG. 9A
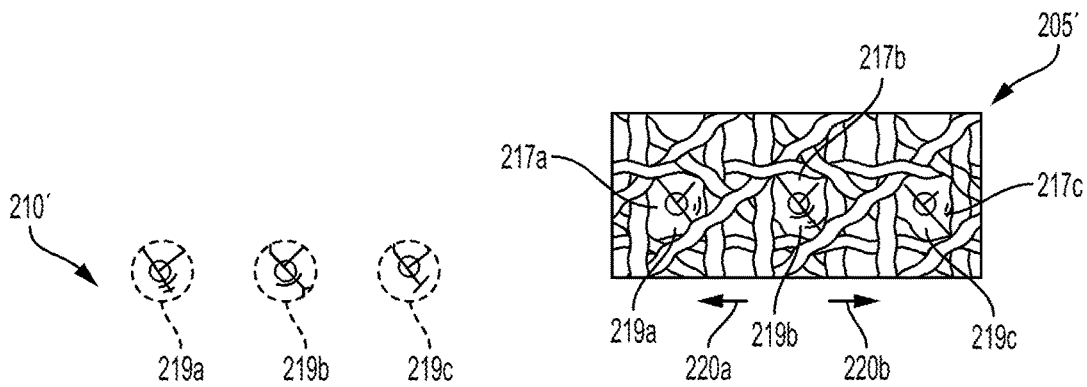
FIG. 9B
FIG. 9C

ADJUNCT MATERIAL WITH MATING FEATURES

FIELD

The present disclosure relates generally to adjunct materials used in conjunction with an end effector of a surgical instrument.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

In some aspects, an end effector for a surgical instrument is provided that in some embodiments includes a first jaw and a second jaw that are configured to clamp tissue therebetween. The first jaw has a cartridge with a plurality of staple cavities configured to seat staples therein, the staple cavities opening on a tissue-facing surface of the cartridge. The second jaw opposing the first jaw has an anvil with a plurality of staple forming cavities formed on a tissue-facing surface thereof. The end effector also includes a plurality of male features formed on a tissue-facing surface of at least one jaw of the first and second jaws, an adjunct material configured to be releasably retained on the at least one jaw, and at least one attachment feature configured to releasably retain the adjunct material on the at least one jaw. The adjunct material includes a plurality of female features, with each female feature being configured to encompass a corresponding at least one of the male features in a clearance fit such that the adjunct material is able to move with respect to the jaw on which it is mounted at least in a first plane parallel to the tissue-facing surface.

The end effector can vary in many different ways. For example, the male features can be formed along at least one of long sides of the at least one jaw. The female features can include openings formed in the adjunct material. In some embodiments, the female features are oversized with respect to the corresponding male features such that male features encompassed by female features are not effective to retain the adjunct material in a second plane that is perpendicular to the first plane. In some embodiments, the at least one attachment feature is or includes adhesive disposed on at least a portion of a surface of the adjunct material facing the at least one jaw.

In some embodiments, at least one of the female features is configured such that a single female feature can encompass more than one male feature. In some embodiments, at least some of the plurality of male features are or include projections extending from the tissue-facing surface of the at least one jaw and configured to mate with respective female features. The projections can be tapered in a direction that is perpendicular to a longitudinal axis of the at least one jaw.

In some embodiments, the adjunct material has a backing layer non-removably attached thereto on a side thereof facing the at least one jaw, and the female features are or include openings formed in the backing layer. At least one of the openings can be configured such that a single opening can encompass more than one male feature.

In other aspects, an adjunct material configured to be releasably retained on a jaw of an end effector for a surgical instrument is provided that in some embodiments includes a plurality of female features and at least one attachment feature configured to releasably retain the adjunct material on the jaw. The plurality of female features are configured to surround corresponding male features formed on a tissue-facing surface of the jaw such that the adjunct material is able to move with respect to the male features in at least a first plane that is parallel to a tissue-facing surface of the jaw on which the adjunct material is mounted.

The adjunct material can vary in many different ways. For example, the jaw on which the adjunct material can be releasably retained can include or can be a cartridge with a plurality of staple cavities configured to seat staples therein formed on a tissue-facing surface of the cartridge. As another example, at least one of the female features can be configured such that a single female feature can surround more than one male feature. In some embodiments, the at least one attachment feature is or includes adhesive disposed on at least a portion of a surface of the adjunct material facing the jaw.

In some embodiments, adjunct material further includes a backing layer non-removably attached to the adjunct material on a side thereof facing the jaw, and the female features are or include openings formed in the backing layer. At least one of the openings can be configured such that a single opening can surround more than one male feature.

In yet other aspects, an end effector for a surgical instrument is provided that in some embodiments includes a first jaw and a second jaw that are configured to clamp tissue therebetween. The first jaw has a cartridge with a plurality of staple cavities configured to seat staples therein, the staple cavities opening on a tissue-facing surface of the cartridge. The second jaw opposing the first jaw has an anvil with a plurality of staple forming cavities formed on a tissue-facing surface thereof. The end effector also includes a plurality of male features formed on a tissue-facing surface of at least one jaw of the first and second jaws, an adjunct material formed from at least partially expandable material and configured to be releasably retained on the at least one jaw, and at least one attachment feature configured to releasably retain the adjunct material on the at least one jaw in a fixed position with respect to the at least one jaw. The adjunct material includes a plurality of female features formed by expandable openings between fibers of the expandable material, with each female feature being able to encompass a corresponding at least one of the male features in a clearance fit such that the adjunct material is able to move with respect to the jaw on which it is mounted at least in a first plane parallel to the tissue-facing surface.

The end effector can vary in many different ways. For example, each of the expandable openings can form a female feature when a corresponding male feature is received in the expandable opening such that the expandable opening is expanded around at least a portion of the male feature. As another example, at least a portion of the expandable material can include fibers forming a pattern such that the expandable openings are formed in the fibers at locations of the adjunct material corresponding to locations of the male features formed on the at least one jaw.

BRIEF DESCRIPTION OF DRAWINGS

This disclosure will be more fully understood from the following detailed description taken in conjunction with the accompanying drawings, in which:

FIG. 8 is a perspective view of a distal portion of an end effector having an adjunct material releasably mounted thereon in accordance with the described techniques;

FIG. 9A is a top view of a portion of an adjunct material having "non-retaining" female features used in accordance with the described techniques;

FIG. 9B is a top view of "non-retaining" male features that can be formed on a jaw for mating with the adjunct material of FIG. 9A, in accordance with the described techniques;

FIG. 9C is a top view of the adjunct material of FIG. 9A having its "non-retaining" female features encompassing the "non-retaining" male features of FIG. 9B;

DETAILED DESCRIPTION

Figure 1:
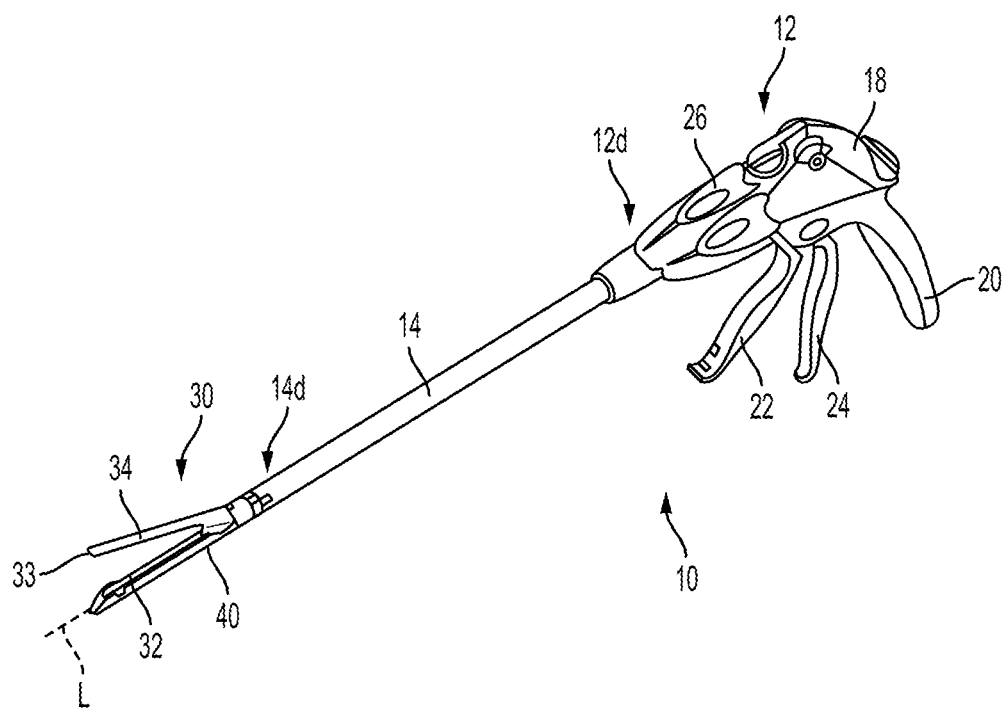
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example, linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be on a variety of tissues in a variety of different surgical procedures, for example in thoracic surgery or in gastric surgery.

Figure 2:
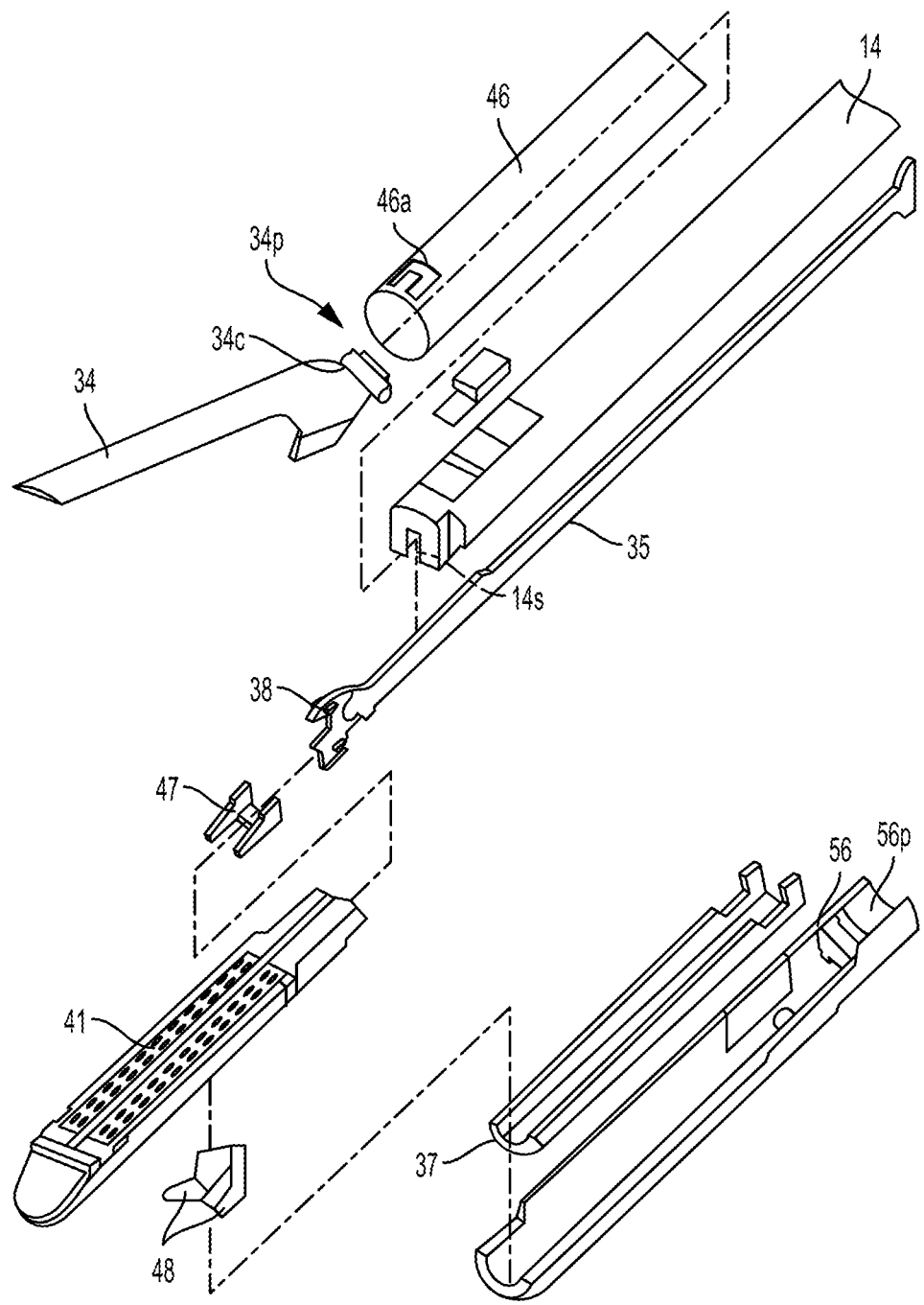
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12*d* of the handle assembly 12, and an end effector 30 at a distal end 14*d* of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12*d* thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
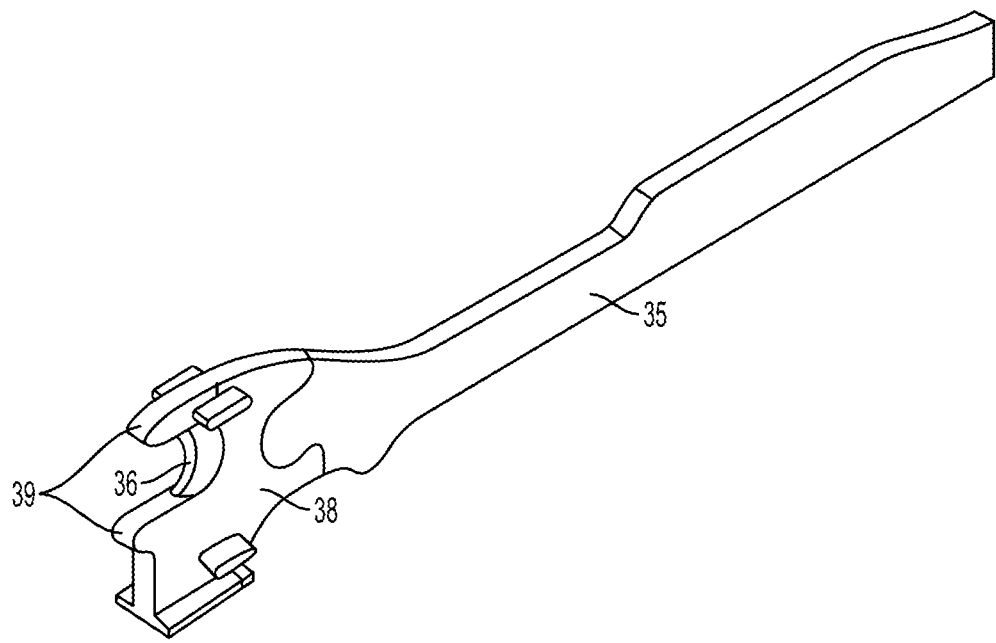
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
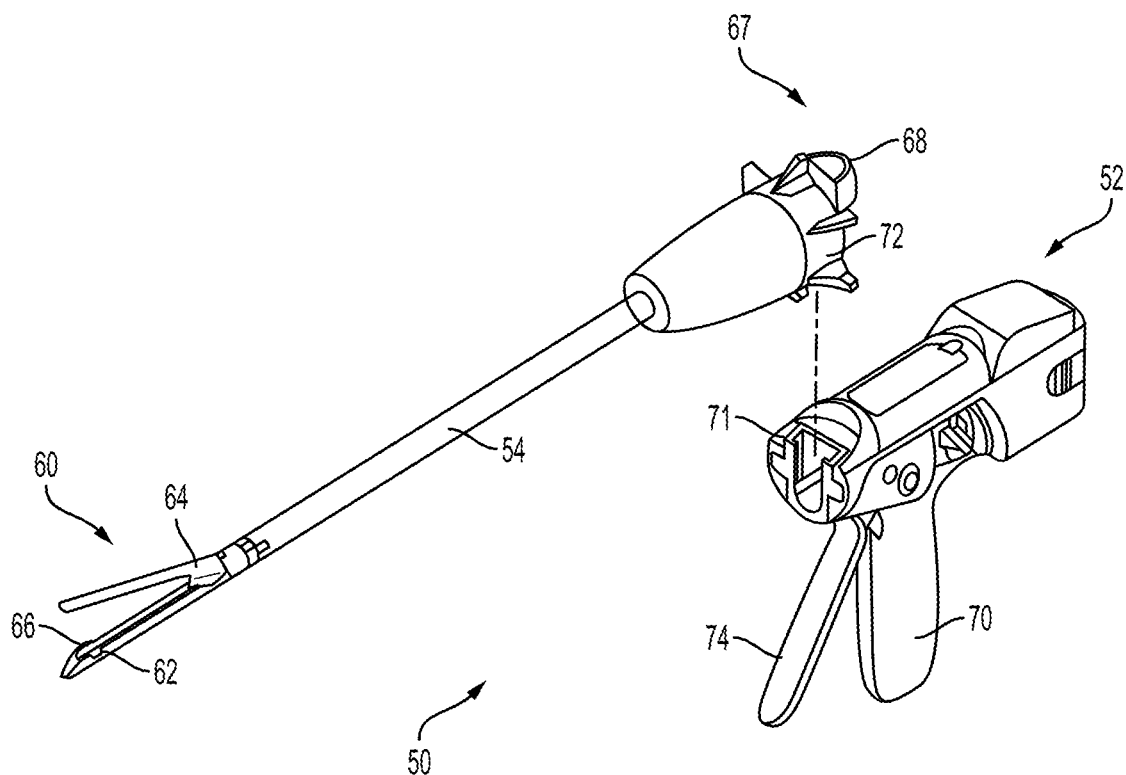
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
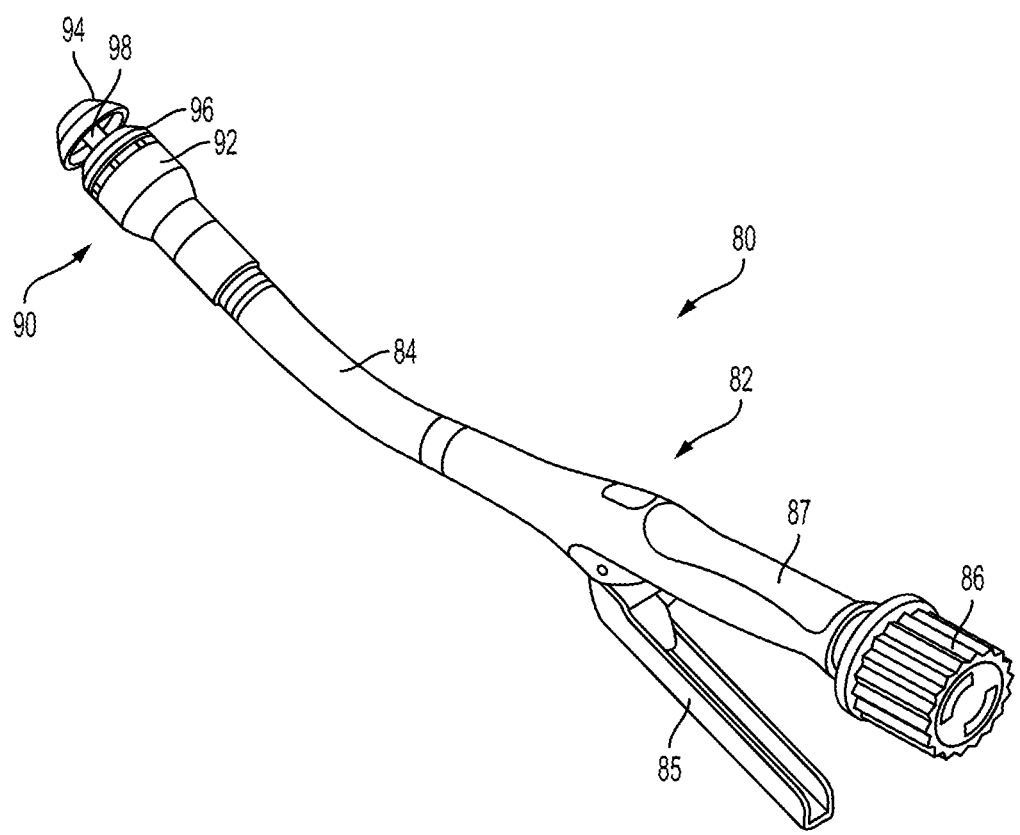
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 98 can be disposed within the cartridge assembly 92 and extend distally outside of the cartridge assembly 92, terminating in a distal mating feature. The second portion of the shaft 98 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film made from any suitable material or a combination of materials discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjuncts that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Implementations

In some implementations, an adjunct or adjunct material can be configured to be releasably retained on a jaw of an end effector for a surgical instrument using different types of features. Specifically, an adjunct material is provided that includes features for releasably attaching the adjunct material to the end effector and features for preventing stretching and/or displacement of the adjunct material as it is transferred to a treatment site in a patient.

The features for attaching the adjunct material to the end effector can be referred to as "retaining" features that are formed on the adjunct such that it can mate with respective features formed on the jaw (an anvil or a cartridge), to releasably retain the adjunct on the jaw. The adjunct is releasably retained on the jaw such that the adjunct remains attached to the jaw until the adjunct is applied to a treatment site. The adjunct additionally includes features that can be referred to as "non-retaining" features that are configured to mate with respective features on the jaw on which the adjunct is mounted such that the adjunct is able to move at least in a plane parallel to the tissue-facing surface. Such "non-retaining" features allow avoiding stretching, sliding off, and/or displacement of the adjunct material from its proper position at a treatment site to which the adjunct material is delivered when the staples are deployed. The adjunct is configured to be positioned on a jaw such that it is aligned with the staple pattern such that the staples, when ejected, penetrate the adjunct at desired locations.

When an end effector is deployed and tissue is clamped between the jaws such that the jaws apply force thereto, squeeze the tissue, and cause it to be penetrated by the deployed staples, the tissue is deformed. For example, portions of the tissue may flow out under the load and can form enlarged areas, which can cause the adjunct to be stretched and displaced from its intended position at the treatment site. This misalignment and displacement of the adjunct can negatively affect the proper reinforcement and/ or treatment of the tissue at the surgical site with the adjunct material. Accordingly, the described techniques provide an adjunct material that includes features that prevent the undesirable stretching and/or displacement of the adjunct material. Such features of the adjunct can mate with complementary features formed on a jaw of an end effector on which the adjunct material is mounted.

In general, in the described implementations, a jaw of the end effector includes a plurality of male features formed on a tissue-facing surface of the jaw. The adjunct material can have a plurality of female features, with each female feature being able to encompass a corresponding one of the male features in a clearance fit such that the adjunct material is able to move with respect to the jaw on which it is mounted at least in a first plane parallel to the tissue-facing surface of the jaw. In this way, these "non-retaining" female and male features limit movement of the adjunct laterally and longitudinally (i.e. in the x and y directions), while not limiting movement of the adjunct in a vertical direction (i.e. in the z direction), which causes the adjunct to remain properly positioned during staple deployment at a treatment site.

The adjunct material also has at least one attachment feature configured to releasably retain the adjunct material on the at least one jaw. Such "retaining" features releasably retain the adjunct with respect to a tissue-facing surface of the jaw until the adjunct is caused to be transferred to the treatment site. Thus, the retaining features can be used to retain the adjunct on the jaw in a substantially non-movable manner. As the staples are deployed by being ejected from an end effector's cartridge, the staples cause the adjunct material to be separated from the jaw to become attached to the tissue with the staples.

Figure 6:
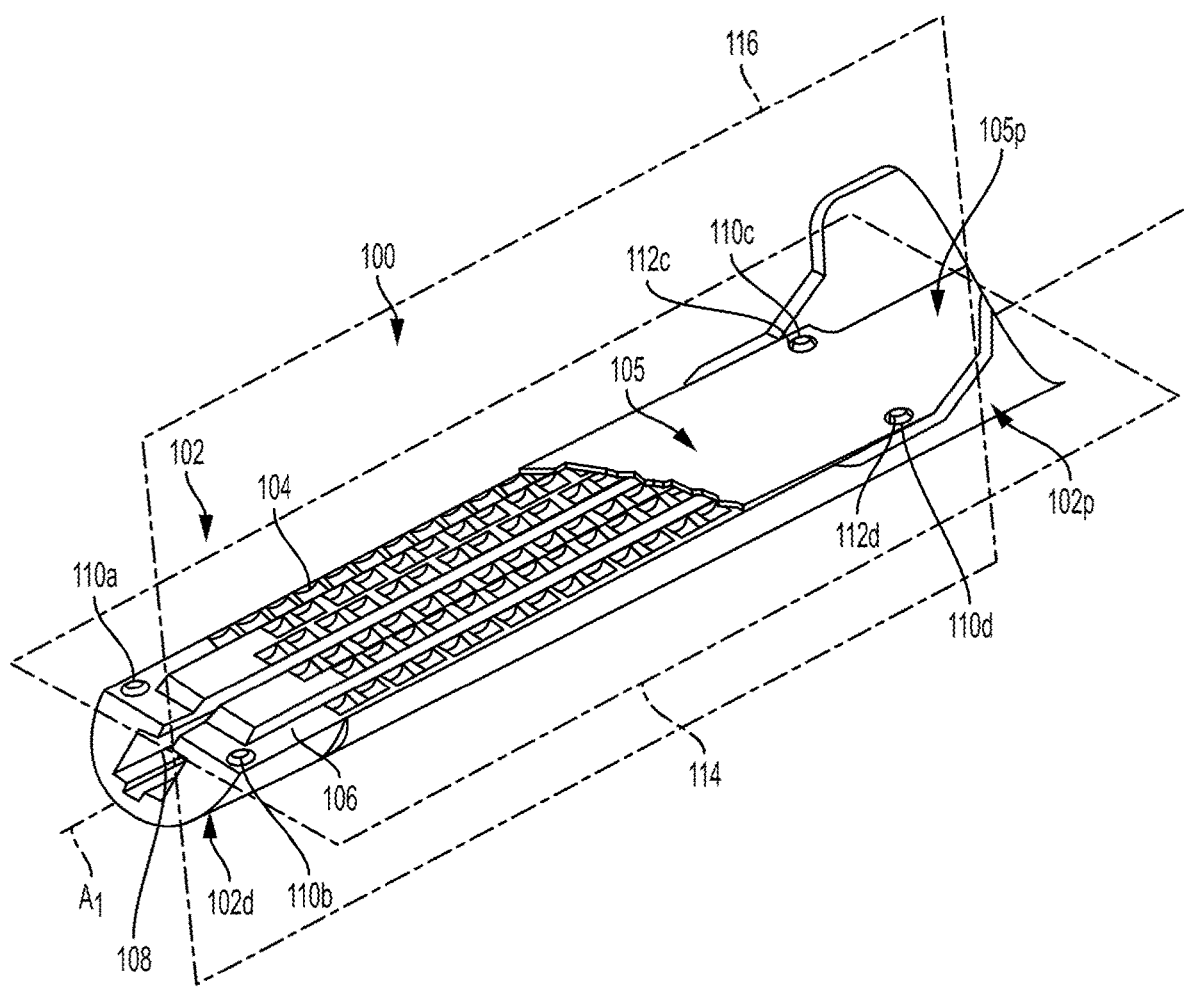
FIG. 6 is a perspective, partial cut-away view of a jaw of an end effector having an adjunct material releasably mounted thereon in accordance with the described techniques.

FIG. 6 illustrates an example of a portion of the end effector 100 having first and second opposed jaws configured to clamp tissue therebetween, in accordance with the described techniques. The end effector 100 can be used with any suitable surgical instrument, for example, a linear surgical stapler (e.g., stapler 10 in FIG. 1, stapler 50 in FIG. 4, or any other surgical stapler) which can be suitable for use with at least one adjunct. The end effector 100, only a portion of which (an upper jaw or anvil 102) is shown in FIG. 6, can be coupled to a distal end of a shaft of the surgical stapler (not shown). As shown in FIG. 6, the anvil 102 has a plurality of staple-forming pockets or cavities 104 formed on a tissue-facing surface 106 of the anvil 102. The staple-forming cavities 104 form a certain pattern on the surface of the anvil 102 which corresponds to a pattern of staple-holding cavities in the cartridge of the end effector 100 (not shown in FIG. 6). The anvil 102 includes an anvil knife channel 108 extending between distal and proximal ends 102d, 102p of the anvil 102. The anvil knife channel 108 is configured to receive a cutting element (e.g., a knife) as the cutting element moves distally through a cartridge knife slot in the staple cartridge.

The end effector 100 includes an adjunct material 105 mounted thereon, a portion of which is shown in FIG. 6 for illustration purposes only. In the example illustrated, the generally rectangular adjunct material 105 includes both retaining and non-retaining features for mating with the anvil of the end effector, as discussed below. It should be appreciated that the anvil 102 is shown by way of example, as the adjunct material can also be mounted on a cartridge using the described techniques. Further, in some embodiments, both anvil and cartridge of an end effector have respective adjunct materials releasably mated thereto using both retaining and non-retaining features in accordance with the described techniques.

As shown in FIG. 6, the anvil 102 includes non-retaining features in the form of male features, such as, in this example, four posts or projections 110a, 110b, 110c, 110d formed on the tissue-facing surface 106 of the anvil 102. As also shown in FIG. 6, the adjunct material 105 also has non-retaining features such as female features in the form of openings configured to encompass corresponding male features in a clearance fit. Because the adjunct material 105 is shown only partially in FIG. 6, two openings 112c, 112d in the adjunct material 105 formed at a proximal end 105p are shown. It should be appreciated, however, that, though not shown, the adjunct material 105 also includes two other openings at a distal end thereof that correspond to the projections 110a, 110b formed on the tissue-facing surface 106 of the anvil 102 at the anvil's distal end 102d.

Figure 7:
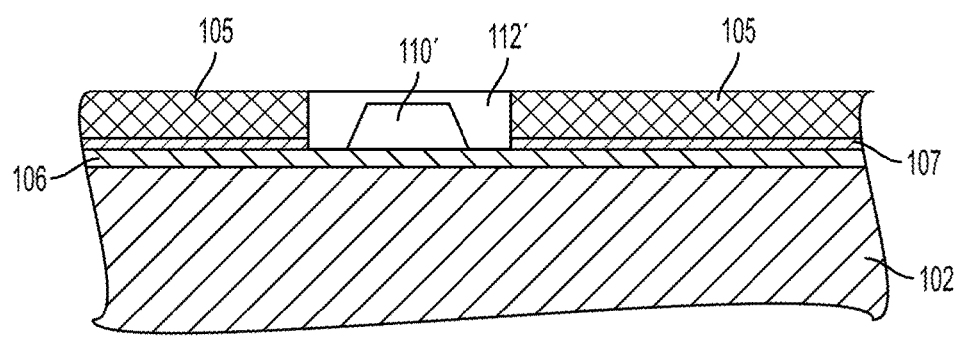
FIG. 7 is a cross-sectional view of a portion of the jaw of FIG. 6 with the adjunct material.

The adjunct material 105 also has one or more retaining features that releasably retain the adjunct material 105 on the jaw 102. In the illustrated example, such features are in the form of a layer 107 of an adhesive material disposed on the jaw-facing surface of the adjunct material 195, as shown in FIG. 7. The adhesive material layer 107 can be formed on the entirety of the adjunct material 105 or it can be disposed on one or more portions of the adjunct material 105. The adhesive material layer 107 can be formed from any suitable material. For example, the adhesive material can be polydioxanone (PDO), a low molecular weight polyethylene glycol (PEG) or any other material (or a combination of materials) that can be used to attach the adjunct to the jaw. In some embodiments, the adhesive material can be a bioabsorbable and/or biodegradable pressure sensitive adhesive.

The female features of the adjunct material 105 and the male features formed on the anvil 102 can have many different configurations and the female and male features can mate in a variety of different ways. In this example, the female features of the adjunct material 105 in the form of openings are configured to encompass the male features in the form of projections formed on the anvil 102 in a clearance fit such that the adjunct material 105 is able to move with respect to the anvil 102 at least in a first plane 114 parallel to the tissue-facing surface 106 of the anvil 102, which is schematically shown in FIG. 6. It should be appreciated, however, that the movement of the adjunct material 105 in the first plane 114 is restricted to the extent that corresponds to a degree of the clearance fit between the female and male features.

As shown in FIG. 7 illustrating a portion of the end effector 100, the projection 110', representing the projections 110a, 110b, 110c, 110d formed on the tissue-facing surface 106 of the anvil 102, is tapered in a direction that is perpendicular to a longitudinal axis A1 of the jaw 102. As further shown in FIG. 7 illustrating a portion of the end effector 100, an opening 112' in the adjunct material 105 (e.g., any of the openings 112, 112d, or other openings) is oversized with respect to a corresponding projection 110' (e.g., any of the anvil's projections 110a, 110b, 110c, 110d) formed on the anvil 102. As a result, the opening 112' encompasses the projection 110' in a clearance fit such that the adjunct material 105 is able to move with respect to the anvil 102 at least in the first plane 114 shown in FIG. 6. When the opening 112' is generally round in shape, as in the illustrated example, its diameter is larger than a largest dimension of the projection 110' in the plane parallel to a plane of the tissue-contacting surface of the jaw.

The configuration and size of the female feature in the form of the opening 112' is such that the male feature in the form of the projection 110' encompassed by opening 112' is not effective to retain the adjunct material 105 in a second plane 116 that is perpendicular to the first plane 114. Thus, the projection 110' is encompassed by the opening 112' such that, if the jaw 102 with the adjunct 105 mounted thereon were to be turned upside down, and if the projection 110' and the opening 112' were the only features used to position the adjunct 105 over the jaw (which is not the case), the adjunct 105 would slide off the jaw 102 with little or no force. It should be appreciated that the planes 114, 116 are referred to as "first" and "second" for purposes of description only, and not to indicate any particular order.

As mentioned above, the adjunct material 105 and the female features formed thereon can have various configurations. In the example illustrated, the openings (e.g., the openings 112c, 112d shown in FIG. 6) in the adjunct material 105 are generally circular in shape and they have a diameter that allows them to encompass the projections (e.g., the projections 112c, 112d) formed on the jaw 102 in a clearance fit. However, it should be appreciated that the adjunct material 105 can have openings having other shapes, which can be different from circular (e.g., oval, rectangular, square, or irregular shapes). Also, the adjunct material can include openings having the same size, or openings of different sizes and/or shapes can be formed in the adjunct material.

The male features, such as the projections 110a, 110b, 110c, 110d formed on the tissue-facing surface 106 of the anvil 102, can be formed at any suitable locations on the anvil 102. The projections can be formed within an area of the tissue-facing surface 106 occupied by the staple-forming pockets 104, or the projections can be formed outside of this area. Thus, in the example of FIG. 6, the projections 110a, 110b formed at the distal end 102d of the anvil 102 are offset distally from the staple-forming pockets 104. The projections 110c, 110d formed at the proximal end 102p of the anvil 102 can be formed within the anvil's area having the staple-forming pockets 104. However, in some embodiments, the projections 110c, 110d can be formed on the area of the anvil 102 outside of the area having the staple-forming pockets 104.

In some implementations, as mentioned above, the projections on the tissue-facing surface of a jaw of the anvil can be formed within the area of the anvil having the staple-forming pockets such that the projections are formed between the staple-forming pockets. The adjunct material used in conjunction with the anvil having such projections can have corresponding female features disposed at locations of the adjunct material such that the female features can encompass the male features in a clearance fit. Furthermore, a cartridge of an end effector can have male features formed within the cartridge's area having the staple pockets (e.g., between the pockets), of the male features can be formed outside of the area having the staple pockets.

A jaw of an end effector can have any suitable number of male features configured to mate with corresponding adjunct's female features using the described techniques— in a non-retaining manner. The four projections 110a, 110b, 110c, 110d formed on the tissue-facing surface 106 of the anvil 102 are shown in FIG. 6 by way of example only. Thus, one, two, three, or more than four projections configured to mate with corresponding female features formed on the adjunct. In embodiments in which one projection is used, it can be in the form of an elongate, narrow feature, such as a rib or a slot. Alternatively, if the adjunct is configured to be constrained proximally by the end effector (e.g., between the tissue stops of the anvil), a single distal attachment point may be sufficient to apply the adjunct to the jaw. Furthermore, in some embodiments, at least one of the female features can be configured such that a single female feature encompasses more than one male feature. For example, one opening formed in the adjunct material can encompass in a clearance fit two or more male features formed on an anvil or on a cartridge.

The non-retaining male and female features (i.e., the features configured to mate such that an adjunct can move with respect to the jaw on which it is mounted at least in the first plane parallel to the tissue-facing surface, and such that the adjunct is not retained in the second plane that is perpendicular to the first plane) can have various configurations. Thus, the projections and openings are shown in FIGS. 6 and 7 by way of example only.

It should be appreciated that retaining attachment features (i.e., features configured to retain the adjunct with respect to the jaw on which it is mounted such that the adjunct cannot move in the first and second planes and can only be separated from the jaw when the staples are ejected) can also have various configurations. As discussed above, in the example shown in FIGS. 6 and 7, the attachment feature is the adhesive layer 107 formed on the jaw-facing surface of the adjunct. Other attachment feature(s) can be used additionally or alternatively, as the described techniques are not limited to any specific attachment features configured to releasably retain the adjunct on the jaw. For example, the jaw can have one or more projections or other male features that can serve as the attachment features configured to mate with respective female features formed on the adjunct material. In some implementations, the attachment male features formed on the adjunct can be configured to mate with complementary female features formed on the jaw. Furthermore, different types of features (e.g., both female and male or combination(s) thereof) can be formed on the adjunct, which can mate with corresponding features of the jaw. The described techniques are also not limited with respect to a number of the attachment features and to specific locations of the attachment features on the jaw and on the adjunct material.

FIG. 8 illustrates another example of a distal portion of an end effector 200 having features in accordance with the described techniques. The end effector 200 can be used with any suitable surgical instrument. For example, it can be used with a linear surgical stapler, such as stapler 10 in FIG. 1, stapler 50 in FIG. 4, or any other surgical stapler. In this example, a jaw in the form of the cartridge 202 of the end effector 200 having staple pockets 204 formed on a tissue-contacting surface 106 thereof is shown. The staple pockets 204 form several rows along a longitudinal axis A2 of the cartridge 202. The cartridge 202 can be a removable and replaceable cartridge. In some embodiments, the cartridge 202 can be part of a replaceable and disposable loading unit configured to couple distally to a shaft (not shown) of the end effector.

As shown in FIG. 8, the tissue-contacting surface 206 of the cartridge 202 has male features in the form of multiple projections 210 formed along a long side of the cartridge 202. In this example, the projections 210 form two rows on opposite sides of the area of the tissue-contacting surface 106 having the staple pockets 204, with the rows extending parallel to the longitudinal axis A2 of the cartridge 202. Any suitable number of projections can be formed at a suitable distance from one another. The projections 210 can be in the form of posts having a rounded and/or tapered head. It should be appreciated, however, that the projections 210 can have any suitable configurations.

As also shown in FIG. 8, the cartridge 202 can retain thereon an adjunct material 205 having female features configured to mate with the jaw's male features in the form of the projections 210 such that each female feature can encompass a corresponding one of the male features in a clearance fit. In this way, the adjunct material 205 is able to move with respect to the jaw 202 at least in a first plane 214 parallel to the tissue-facing surface 206 of the jaw 202.

In the example of FIG. 8, the adjunct 205 is formed from at least partially stretchable or expandable material formed of fibers such that at least some portions of the adjuncts are relatively loose. For example, the adjunct can be a fiber-based lattice which can be a woven fabric, knitted fabric or non-woven fabric. The adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose.

The expandable material can be, e.g., in the form of a mesh material having fibers forming regular or irregular patterns, or a combination of regular or irregular patterns. The adjunct 205 has a plurality of female features in the form of expandable openings 212 formed between fibers of the expandable material. The openings 212 can be pre-formed in the adjunct material 205 such that they are formed at predetermined locations. For example, the openings 212 can be formed in two rows along opposite long sides of the adjunct material 205, as shown in FIG. 8. In some embodiments, the expandable openings can exist in the adjunct material 205 due to the nature of the fabric from which the adjunct material is formed. As mentioned above, the entire adjunct material or one or more portions thereof can be relatively loosely interconnected, and such loosely interconnected portions can have openings therein. In such embodiments, the male features formed on the jaw can "find" openings in the adjunct to mate with when the adjunct is placed over the jaw.

Regardless of the specific way in which the female features are formed in the adjunct material, the adjunct material can mate with the male features formed on the jaw because the expandable material stretches (e.g., its fibers separate) and thus enlarges in places where the male features are inserted at least through the mesh. FIGS. 9A, 9B, and 9C illustrate an example of openings 212' in an adjunct material 205' that can encompass posts or projections 210' formed on a jaw, such as the cartridge 202 or other jaw (which can be an anvil).

As shown in FIG. 9A, openings 212' in an adjunct material 205', three of which are labeled as openings 217a, 217b, 217c, can be present in the expandable material forming the adjunct material 205' due to the way in which the fibers of the adjunct material are interwoven. The openings 217a, 217b, 217c exist between the interwoven fibers of the adjunct material 205' and each can be expanded, enlarged, or deformed when it receives a respective projection therein. FIG. 9B illustrates by way of example of three projections 219a, 219b, 219c of the multiple projections that can be formed on the jaw, such as the cartridge 202 in FIG. 8 or other jaw.

When the adjunct material 205' is laid over the jaw, the projections 219a, 219b, 219c are received within the openings 217a, 217b, 217c such that the material forming the adjunct material 205' stretches over the projections 219a, 219b, 219c in direction indicated by arrows 220a, 220b, as shown in FIG. 9C. The property of the material is such that it is stretched and/or deformed so that the adjunct material 205' is able to move with respect to the jaw at least in a first plane parallel to the tissue-facing surface of the jaw and so that the adjunct material is not retained in a second plane that is perpendicular to the first plane.

In addition to female features described above, the adjunct material 205 in FIG. 8 and the adjunct material 205' shown in FIGS. 9A and 9C also have at least one attachment feature configured to releasably retain the adjunct material on the jaw. The at least one attachment feature can be an adhesive material layer formed over at least a portion of the adjunct material, or any other type of feature(s), such as a male or female feature, or a combination thereof. The at least one attachment feature can be configured to mate with the end effector's jaw on which the adjunct is mounted, in a way corresponding to a type of the attachment feature. For example, when the attachment feature is the adhesive material layer, such adhesive material layer attaches to the jaw due to its adhesive nature. When the attachment feature is one or more openings or projections, they are configured to mate with corresponding projections or openings formed on the jaw.

Regardless of the specific type, number, and location of attachment feature(s) formed on the adjunct material, they are formed to retain the adjunct material on the jaw in three dimensions, such that the adjunct can be separated from the jaw when the staples are ejected from the cartridge. The adjunct's non-retaining features (e.g., various female features described herein), which do not retain the adjunct with respect to the jaw in the plane perpendicular to a plane parallel to the jaw's tissue-contacting surface, are used to prevent stretching of the adjunct material and/or displacement (e.g., slipping or sliding off) of the adjunct from the jaws of the end effector. Thus, unlike the non-retaining adjunct's features that are only used to properly position the adjunct, the attachment features serve to releasably retain the adjunct on the jaw.

Figure 10:
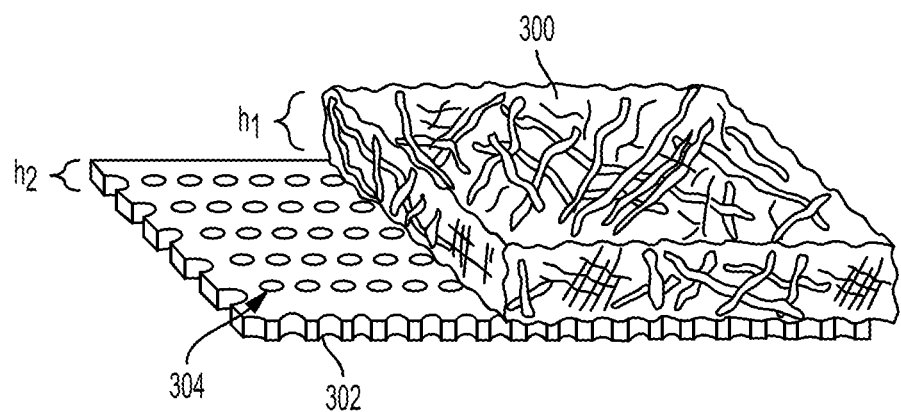
FIG. 10 is a perspective, partial cut-away view of an adjunct material having a backing layer in accordance with the described techniques.
Figure 11:
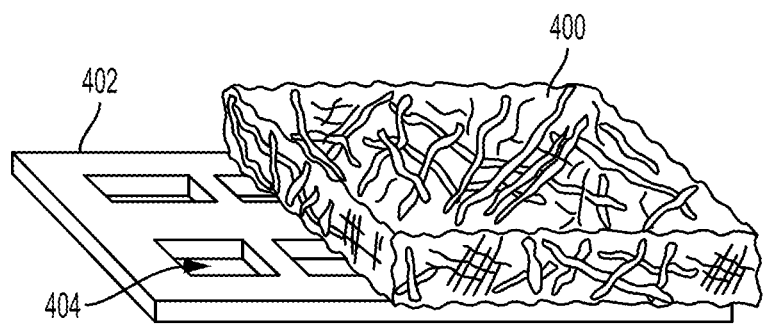
FIG. 11 is a perspective, partial cut-away view of another adjunct material having a backing layer in accordance with the described techniques.

In some embodiments, an adjunct material is formed from fibers and it comprises a backing layer non-removably attached thereto on a side of the adjunct material facing the jaw. The fibers can be a mesh, nonwoven fibers, or any other type(s) of fibers. The backing layer can have female features formed thereon for mating with respective male features formed on the jaw on which the adjunct material is mounted. FIGS. 10 and 11 illustrate example of such adjunct material, with the jaw not shown.

FIG. 10 illustrates an example of an adjunct material 300 in the form of a generally rectangular fiber layer. The adjunct material 300 has a backing layer 302 non-removably attached thereto on a side of the adjunct material facing the jaw of an end effector. As shown in FIG. 10, the backing layer 302 has a plurality of female features in the form of openings 304 formed thereon. The openings 304 can mate with corresponding male features of the jaw (e.g., a cartridge or anvil). In this example, the openings 304 are configured to mate with the male features such that not every opening mates with the jaw. Thus, a pattern and/or number of male features formed on the jaw may be different from a pattern and/or number of female features formed on the adjunct material. For example, the jaw can have fewer male features (e.g., projections such as projections 110 (FIG. 6), projections 210 (FIG. 8), or any other male features) than the number of openings. In this way, for example, only some of the openings 304 (which are oversized with respect to the male features) may surround respective male features. Thus, there is no requirement that specific openings surround specific male features. The adjunct material 300 with multiple openings formed therein can thus be easily positioned over the jaw and the male features "find" openings that can surround the male features. The number of the male features can be selected such that it is sufficient to prevent displacement of the adjunct material from the end effector's jaw(s), in accordance with the described techniques.

The openings 304 can have any suitable configuration. For example, while generally circular openings 304 are shown in FIG. 10, the openings can be oval, rectangular, square, or they have can other regular or irregular shapes. Any suitable number of openings can be formed in any suitable pattern(s).

The backing layer 302 can be formed from any suitable biodegradable and/or bioabsorbable material, such as, for example, polydioxanone (PDO) or any other suitable polymeric material(s). The material can be selected such that it biodegrades and/or bioabsorbs faster than the adjunct material 320. As shown in FIG. 10, the backing layer 302 has a thickness that is smaller than that of the adjunct material 320. For example, in some embodiments, the height or thickness h1 of the adjunct material 320 can be from about 0.004 inches to about 0.020 inches, whereas the height or thickness h2 of the backing layer 302 can be from about 0.0002 inches to about 0.0012 inches. However, in some embodiments, the thickness h1 of the adjunct material can be greater—e.g., from about 0.01 inches to about 0.150 inches. The thickness h1 of the adjunct material, as well as the thickness h2 of the backing layer, can vary within other suitable ranges.

FIG. 11 illustrates another example of an adjunct material 400 in the form of a generally rectangular fiber layer. The adjunct material 400 has a backing layer 402 non-removably attached thereto on a side of the adjunct material 400 facing a jaw of an end effector (not shown). As shown in FIG. 11, the backing layer 402 has a plurality of female features in the form of openings 404 formed thereon. The openings 404 can mate with corresponding male features of the jaw (e.g., a cartridge or anvil). The openings 404 can be configured to mate with the male features such that one opening can surround two or more male features. Thus, as illustrated in FIG. 11, the backing layer 402 has several (e.g., two, three, or greater than there) openings formed therein each of which can surround more than one male feature (e.g., projections, posts, etc.) formed on the jaw. For example, one opening (or "window") 404 can surround a group of jaw's male features. Also, in some embodiments, only some of the openings 404 will surround two or more male features.

Furthermore, in some embodiments, the backing layer can have one opening. For example, it can be a relatively large opening such that the backing layer can be in the shape of a frame that is coupled to the adjunct material along a perimeter of the adjunct. The frame-shaped backing layer can couple with a jaw via male features disposed on the jaw in a certain manner. For example, four or more male features (e.g., posts) can be disposed at opposed sides at the distal and proximal ends of the jaw and the frame-shaped backing layer, with the adjunct coupled thereto, can be retained on the jaw via such features received within the opening in the backing layer.

The openings 404 can have any suitable configuration and size. For example, as shown in FIG. 11, the openings 404 can be rectangular. However, they can alternatively be square, round, oval, etc. Also, the adjunct material can have openings of different sizes and/or shapes. The backing layer 402 can be formed from one or more materials similar to the backing layer 302 in FIG. 10.

Furthermore, although not shown separately in FIGS. 10 and 11, each of the adjunct materials 300 and 400 also includes one or more attachment features configured to releasable retain the adjunct material on the jaw. The attachment feature(s) can be in the form of an adhesive material layer, female, male, or other type of features that are used to retain the adjunct material on the jaw in all three dimensions. Furthermore, in some embodiments, the material from which the backing layer (e.g., backing layer 302 in FIG. 10 or backing layer 402 in FIG. 11) is formed can be an adhesive material serving as an attachment layer. The adhesive material can be any suitable polymer, such as polydioxanone (PDO), a low molecular weight polyethylene glycol (PEG) or any other material (or a combination of materials) that can be used to attach the adjunct to the jaw. In some embodiments, the adhesive material can be a bioabsorbable and/or biodegradable pressure sensitive adhesive.

In the example of FIGS. 10 and 11, the backing layer non-removably attached to the adjunct material on jaw-facing surface thereof is formed substantially over entire surface of the adjunct material. In some embodiments, the backing layer can be in the form of discrete portions. In this way, while some portions of the adjunct material can be prevented from being stretched, other portions can be stretched once the adjunct material is applied to tissue at a treatment site. The adjunct material can thus move with the tissue at which it is implanted when the tissue moves, while remaining being coupled to the tissue. This may be desirable when tissue such as, for example, lung is being treated, which needs to be able to expand and contract to perform its function. Allowing the implanted adjunct material to stretch to some degree allows the tissue to heal appropriately.

Figure 12:
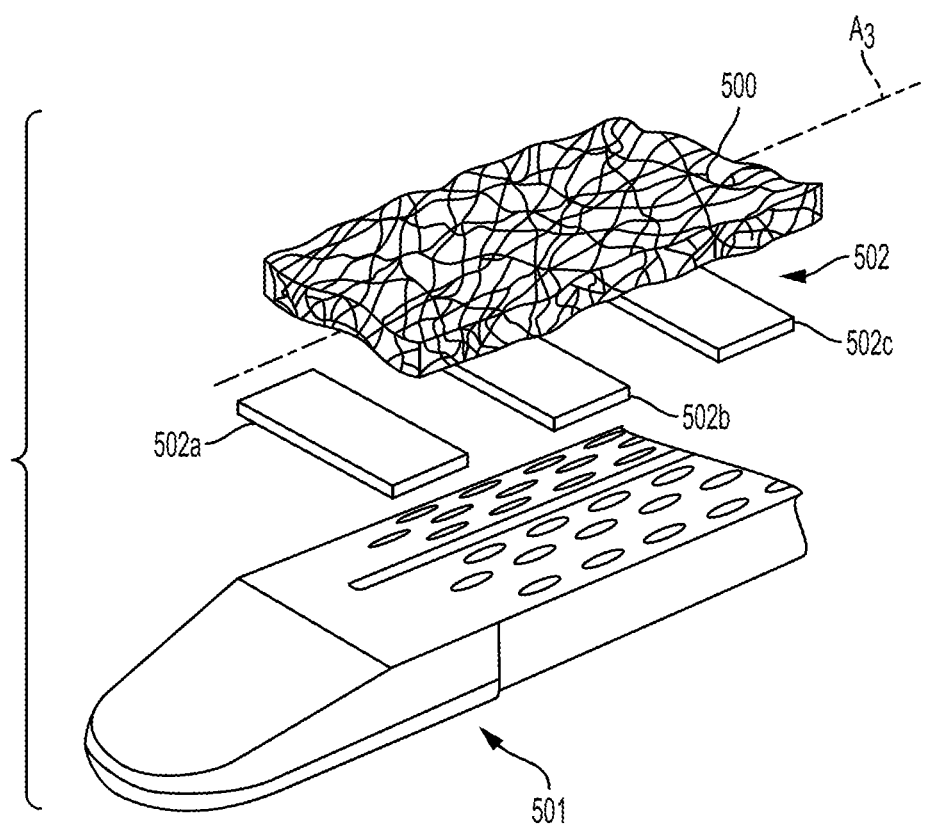
FIG. 12 is a perspective, partially exploded view of a distal portion of a jaw of an end effector and an adjunct material configured to be releasably mounted on the jaw in accordance with the described techniques.
Figure 13:
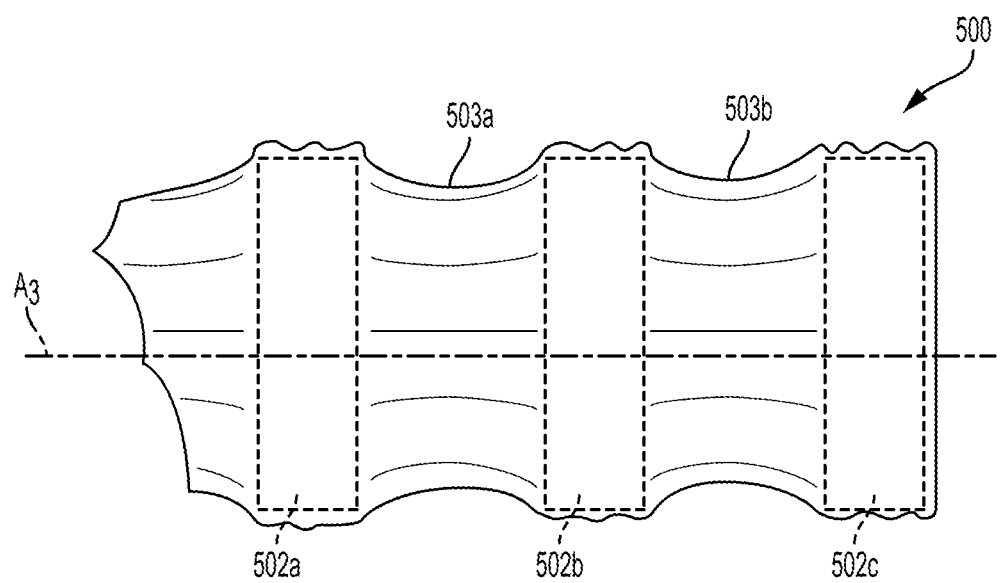
FIG. 13 is a bottom view of the adjunct material of FIG. 12, illustrating the adjunct material when it is retained at a treatment site in a patient.

FIGS. 12 and 13 illustrate an example of an adjunct material 500 to be disposed over a jaw 501 which is, in this example, a cartridge. The adjunct material 500 can however be disposed over an anvil as well. As shown in FIG. 12, the adjunct material 500 has discrete portion or panels 502, 502b, 502c forming a backing side or layer 502. As shown, the panels 502, 502b, 502c non-removably attached to the adjunct material 500 are disposed perpendicular to a longitudinal axis A3 of the adjunct material 500. It should be appreciated that three panels 502, 502b, 502c are shown by way of example only, as two or greater than three panels can span the adjunct material 500 along a short side thereof.

The adjunct material 500 can be formed from any suitable material described herein, which can be a mesh or a non-woven material. The backing layer 502 can also be formed from any suitable material, such as a biodegradable and/or bioabsorbable material, e.g., polydioxanone (PDO) or any other suitable polymeric material(s). The material can be selected such that it biodegrades and/or bioabsorbs faster than the adjunct material 500. The backing layer 502 has a thickness that is smaller than that of the adjunct material 500. For example, in some embodiments, the height or thickness of the adjunct material 500 can be from about 0.004 inches to about 0.020 inches, whereas the height or thickness of the backing layer 502 can be from about 0.0002 inches to about 0.0012 inches.

As shown in FIG. 13, illustrating by way of example a back side of the adjunct material 500 with the panels 502, 502b, 502c when the adjunct material 500 is retained at the treatment side (the staples and tissue are not shown), the panels 502, 502b, 502c prevent stretching of the portions of the adjunct material 500 to which the panels 502, 502b, 502c are attached. As also shown, the portions of the adjunct material 500 between the panels 502, 502b, 502c, such as portions 503a, 503b in FIG. 11, can stretch along the longitudinal axis A3 of the adjunct material 500 once implanted on tissue. Thus, while the panels 502, 502*b*, 502*c* prevent undesirable excessive stretching and displacement of the adjunct material 500 at the treatment site, the portions of the adjunct material 500 between the panels allow the adjunct stretching where desired.

It should be appreciated that the number, size, and location of the panels configured to prevent stretching of portions of the adjunct material can be selected to create a desired pattern of areas at which the adjunct is coupled to the jaw (e.g., the areas coupled to the panels) and areas at which the adjunct is allowed to stretch once implanted. In some embodiments, adjunct(s) that are at least partially stretchable at some portions thereof can be used in conjunction with a staple line that can be flexible as described, for example, in the above-mentioned U.S. Pat. Pub. No. 2016/0089142 entitled "Method for Creating a Flexible Staple Line," and filed on Sep. 26, 2014, which is hereby incorporated by reference herein in its entirety. Such implementations can be used for treatment of tissue which contracts and expands, such as lung. Furthermore, in some embodiments, the panels, such as the panels 502, 502*b*, 502*c*, can be aligned with some staples and not others along the longitudinal length of the jaw. Also, when the adjuncts with the backing layer panels are disposed on both jaws of an end effector, the panels formed on the opposed adjuncts can have a pattern (e.g., a complementary pattern) such that a staple, once ejected, passes only through one of the backing layers. The panels and spacing between panels can be selected such that the panels form irregular and non-uniform patterns, and adhesive is applied to the panels.

As in other examples illustrating the described techniques, the adjunct material 500 also includes one or more attachment features which can be in the form of an adhesive material layer formed at the jaw-facing surface of the panels 502, 502*b*, 502*c*. Other attachment features can be formed additionally or alternatively. Furthermore, in some embodiments, the material from which the panels 502, 502*b*, 502*c* are formed can be an adhesive material serving as an attachment layer. The adhesive material can be any suitable polymer, such as polydioxanone (PDO), a low molecular weight polyethylene glycol (PEG) or any other material (or a combination of materials) that can be used to attach the adjunct to the jaw. In some embodiments, the adhesive material can be a bioabsorbable and/or biodegradable pressure sensitive adhesive.

It should be appreciated that the adjunct materials described herein can be used with various types of end effectors that can be used in linear or circular stapler instruments. For example, it can be used in a linear surgical stapler, such as stapler 10 in FIG. 1 or stapler 50 in FIG. 4, or in a circular surgical, such as stapler 80 in FIG. 5, or in any other surgical stapler instrument. Thus, although generally rectangular adjuncts are shown in FIGS. 6, 8, 10, 11, 12, and 13, the adjuncts can be created such that they have a generally circular shape and such that their retaining and non-retaining features are configured for mating with an end effector of a circular stapler instrument. Also, as mentioned above, the adjunct can have or can be associated with various types "retaining" and "non-retaining" features.

Furthermore, the adjunct materials described herein can include one or more medicants which can be releasably incorporated into or associated with adjuncts in many different ways. Also, the adjunct materials can have various other features in addition to the features described herein.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. An end effector for a surgical instrument, comprising:
a first jaw having a cartridge with a plurality of staple cavities configured to seat staples therein, the staple cavities opening on a tissue-facing surface of the cartridge, the tissue-facing surface extending along a first longitudinal axis;
a second jaw opposing the first jaw and having an anvil with a plurality of staple forming cavities formed on a tissue-facing surface thereof, wherein the first and second jaws are configured to clamp tissue therebetween;
an adjunct material configured to be releasably retained on the first jaw, the adjunct material extending along a second longitudinal axis from a first end to a second end; and
a backing layer non-removably attached on a side of the adjunct material that faces the first jaw and positioned on the side of the adjunct material at a distance from at least one of the first end and the second end of the adjunct material, the backing layer being configured to prevent stretching of one or more portions of the adjunct material;
wherein the backing layer is substantially planar with a substantially uniform thickness,
wherein the backing layer has a first length and the adjunct material has a second length that is greater than the first length; and
wherein, when the adjunct material is releasably retained on the first jaw, the backing layer at least partially overlaps the staple cavities of the first jaw and the second longitudinal axis extends parallel to the first longitudinal axis.

2. The end effector of claim 1, wherein the backing layer comprises at least two panels, each panel being attached to a portion of the adjunct material and configured to prevent stretching of its corresponding portion of the adjunct material, and wherein the at least two panels are configured to allow stretching of the remaining portions of the adjunct material.

3. The end effector of claim 2, where the at least two panels are disposed perpendicular to the second longitudinal axis of the adjunct material.

4. The end effector of claim 1, wherein the backing layer has a first thickness and the adjunct material has a second thickness that is greater than the first thickness.

5. The end effector of claim 1, further comprising one or more attachment features configured to releasably retain the adjunct material on the first jaw.

6. The end effector of claim 5, wherein the one or more attachment features are in the form of an adhesive material layer attached to a side of the backing layer that faces the first jaw.

7. The end effector of claim 1, wherein the adjunct material is formed of a mesh or a non-woven material.

8. The end effector of claim 1, wherein the backing layer is formed of a least one of a biodegradable material and a bioabsorbable material.

9. The end effector of claim 1, further comprising a plurality of male features formed on the tissue-facing surface of the first jaw.

10. The end effector of claim 1, wherein the backing layer comprises a plurality of female features.

11. The end effector of claim 10, wherein the plurality of female features comprises openings formed in the backing layer.

12. The end effector of claim 11, wherein at least one of the openings is configured such that a single opening can encompass more than one male feature of a plurality of male features formed on the tissue-facing surface of the first jaw.

13. The end effector of claim 1, wherein the backing layer is formed of an adhesive material.

14. The end effector of claim 1, further comprising an additional adjunct material configured to be releasably retained on the second jaw, and an additional backing layer non-removably attached to the additional adjunct material, the backing layer being configured to prevent stretching of one or more portions of the additional adjunct material.

15. An end effector for a surgical instrument, comprising:
   a first jaw having a cartridge with a plurality of staple cavities configured to seat staples therein, the staple cavities opening on a tissue-facing surface of the cartridge;
   a second jaw opposing the first jaw and having an anvil with a plurality of staple forming cavities formed on a tissue-facing surface thereof, wherein the first and second jaws are configured to clamp tissue therebetween, and wherein the first and second jaws each extend from a distal end to a proximal end and are pivotally coupled to each other at respective proximal ends;
   an adjunct material configured to be releasably retained on the first jaw, the adjunct material extending along a longitudinal axis from a first end to a second end wherein the first end is configured to be positioned proximate to the distal end of the first jaw and the second end is configured to be positioned proximate to the proximal end of the first jaw; and
   a backing layer comprising at least two discrete panels that are completely spaced apart from each other, the backing layer being non-removably attached on a side of the adjunct material that faces the first jaw and positioned on the side of the adjunct material at a distance from at least one of the first end and the second end of the adjunct material, the backing layer being configured to prevent stretching of one or more portions of the adjunct material;
   wherein the backing layer at least partially overlaps the staple cavities of the first jaw when the adjunct material is releasably retained on the first jaw.

16. The end effector of claim 15, wherein each panel being attached to a portion of the adjunct material and configured to prevent stretching of its corresponding portion of the adjunct material, and wherein the at least discrete two panels are configured to allow stretching of the remaining portions of the adjunct material.

17. The end effector of claim 15, further comprising one or more attachment features configured to releasably retain the adjunct material on the first jaw.

18. The end effector of claim 1, wherein the cartridge is configured to be removable from the first jaw and to be replaceable.

19. The end effector of claim 15, wherein the cartridge is configured to be removable from the first jaw and to be replaceable.

20. The end effector of claim 15, wherein the adjunct material is formed of a mesh or a non-woven material.

21. The end effector of claim 15, wherein the backing layer is formed of a least one of a biodegradable material and a bioabsorbable material.

22. The end effector of claim 15, wherein the backing layer has a first thickness and the adjunct material has a second thickness that is greater than the first thickness.

* * * * *